(12) United States Patent
Bonomo (10) Patent No.: US 11,266,791 B2
(45) Date of Patent: Mar. 8, 2022

(54) APPARATUS FOR THE SAFE MANAGEMENT OF HYPODERMIC NEEDLES

(71) Applicant: James Bonomo, Newbury Park, CA (US)

(72) Inventor: James Bonomo, Newbury Park, CA (US)

( * ) Notice: Subject to any disclaimer, the term of this patent is extended or adjusted under 35 U.S.C. 154(b) by 111 days.

(21) Appl. No.: 16/571,096

(22) Filed: Sep. 14, 2019

(65) Prior Publication Data
US 2021/0077746 A1    Mar. 18, 2021

(51) Int. Cl.
*A61M 5/32*    (2006.01)

(52) U.S. Cl.
CPC ........ *A61M 5/3221* (2013.01); *A61M 5/3204* (2013.01)

(58) Field of Classification Search
CPC .. A61M 5/3221; A61M 5/3204; A61M 5/321; A61M 5/3202
See application file for complete search history.

(56) References Cited

U.S. PATENT DOCUMENTS

| 4,742,910 A * | 5/1988 | Staebler | A61M 5/3213 206/365 |
| 5,183,469 A * | 2/1993 | Capaccio | A61M 5/3213 206/365 |
| 6,279,743 B1 * | 8/2001 | Ballard | A61M 5/3213 128/852 |

FOREIGN PATENT DOCUMENTS

| FR | 2729083 A1 * | 7/1996 | .......... A61M 5/3213 |
| WO | WO-2018106680 A1 * | 6/2018 | ......... A61B 50/3001 |

* cited by examiner

*Primary Examiner* — Theodore J Stigell
*Assistant Examiner* — Rachel T. Smith (57) ABSTRACT

An apparatus for the safe removal and replacement of hypodermic needle caps, interchanging of needles, and storage during tasks is disclosed, including a heavy base with space hollowed out to allow for cap gripping mechanism and tunnel for capped needle removal, wherein the base may be slanted slightly towards the user. The friction or mechanical needle cap gripping mechanism may be comprised of rubber, soft plastic, or the like, with a top to secure the cap gripping mechanism in the base. A ramped cone shaped opening is provided in the top to allow for the cap of a capped needle to pass through and be captured by the cap gripping mechanism, and an extended tunnel shaped opening is provided to allow for the re-capped needle to be removed and needles to be interchanged.

5 Claims, 17 Drawing Sheets

APPARATUS FOR THE SAFE MANAGEMENT OF HYPODERMIC NEEDLES

CROSS REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates generally to the field of medical devices and more specifically to a device for the safe removal and replacement of hypodermic needle caps.

Prior technology generally consists of a light plastic device that allows for the connection of one or more caps of hypodermic needles, that with the use of both hands allows for the safe removal and replacement of the needle cap.

A deficiency in the prior technology is the requirement of the usage of both hands for connecting the needle, removal and replacement of the cap, and removing the needle from the device. Another deficiency is that because both hands are required for usage, the cap side hand would still be in danger of a possible stick. Still another deficiency is overall efficiency suffers because of the nature of how the device connects and disconnects from the hypodermic needle cap and the need for both hands during usage.

Another prior technology includes a one-piece disposable design which requires it be affixed to a stationary object for the possibility, though not guaranteed, one handed usage. Another deficiency is that the device wears out, due to the nature of how the captured needle is removed, over time and therefore needs to be replaced.

BRIEF SUMMARY

An object of the description is to allow for the safe removal and replacement of hypodermic needle caps.

Another object of the description is to support one handed usage without the need to affix the device to a stationary object.

Another object of the description is to allow for the interchanging of needles via the integrated needle cap securing channel.

Another object of the description is to allow needle caps to be held/stored while using the needle and allows for one handed re-capping by the user.

Another object of the description is to allow for the storage of needles to allow for related/unrelated tasks to be completed safely.

Another object of the description of the invention is to prevent accidental injection or damage to the operator.

A further object of the description is to prevent contamination.

Yet another object of the description of the invention is to prevent spread of disease.

Still yet another object of the description is to increase efficiency in the uncapping and re-capping of needles.

Another object of the description is to increase efficiency in experimentation requiring the usage of hypodermic needles.

Other objects and advantages of the present invention will become apparent from the following descriptions, taken in connection with the accompanying drawings, wherein, by way of illustration and example, an embodiment of the present invention is disclosed.

In accordance with an aspect of the presented technology, there is disclosed an apparatus for the safe removal and replacement of hypodermic needle caps comprising: a weighted base with space to allow for a cap gripping mechanism and a tunnel with a tunnel lock for capped needle removal and/or interchanging which is slanted slightly towards the user (when the weighted base is so positioned), a replaceable/interchangeable needle cap gripping mechanism, comprised of rubber, soft plastic, or the like, a top to secure the cap gripping mechanism (capture core) in the base, with a channel that allows for one-handed removal, a ramped cone shaped opening in the top to help guide and allow for the cap of a capped needle to pass through and be captured by the cap gripping mechanism (capture core), and an extended tunnel like opening to allow for the re-capped needle to be safely single handedly removed, repeatedly, without accidentally uncapping it.

The device of the present description takes the place of and eliminates the need for the de-capping/re-capping hand in the procedure of removing and replacing the cap of a hypodermic needle, thus removing the possibility of an accidental needle stick, and allows for the safe interchanging of needles, and allows for the safe storage of needles by allowing the user to place an capped/uncapped needle in the stand safely while completing tasks, therefore avoiding accidental needle sticks in between activities.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

Figure 1:
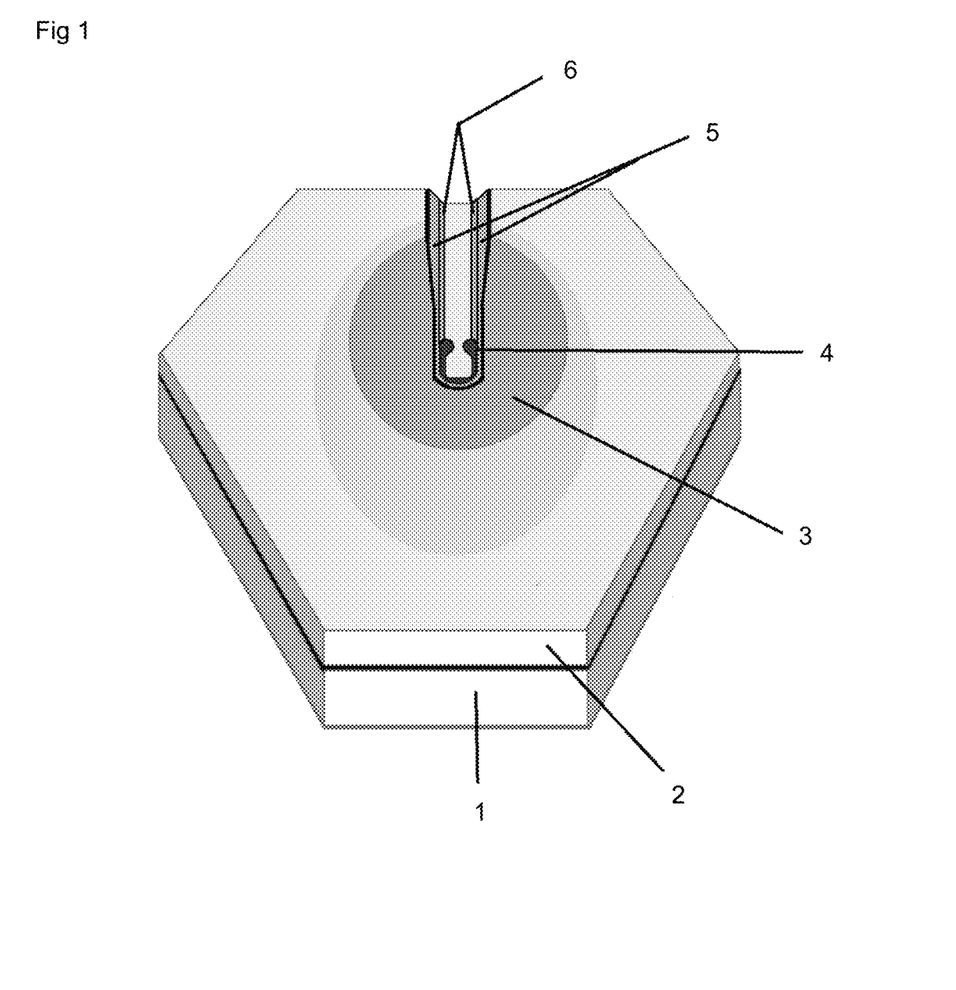
FIG. 1 is a top perspective (front) view of an embodiment of an apparatus in accordance with the present description.
Figure 1A:
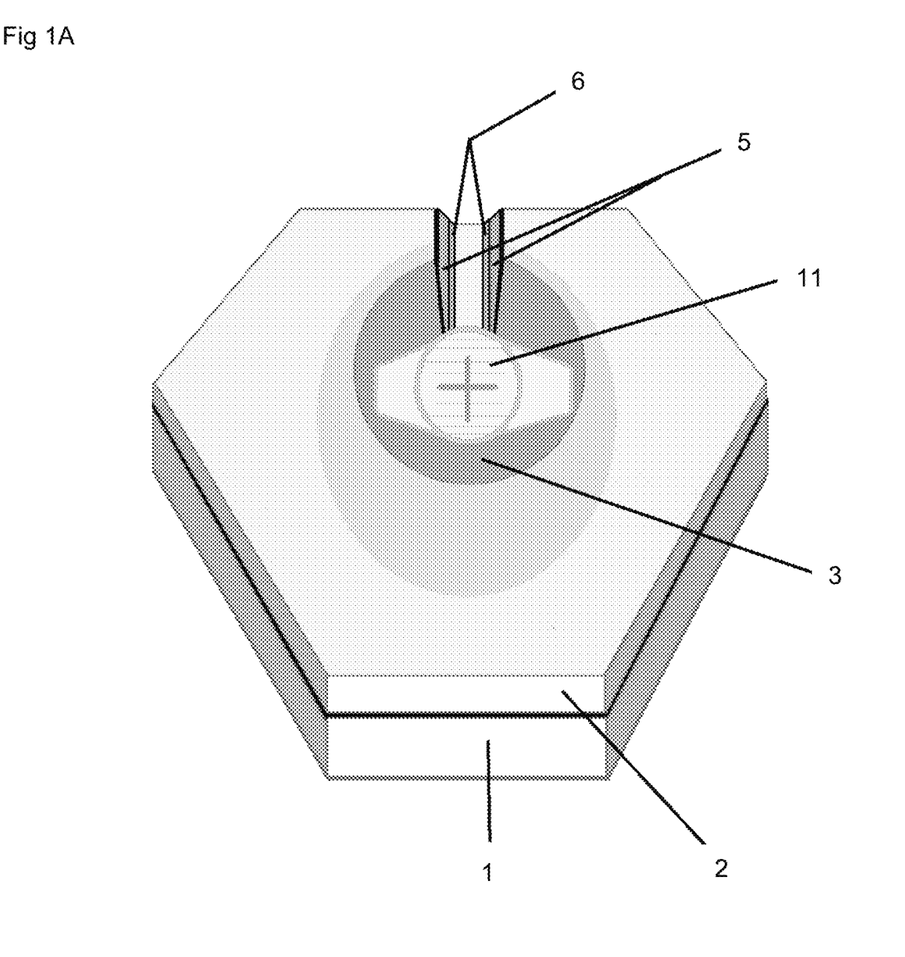
FIG. 1A is the same view as FIG. 1, with the apparatus in use with an entire needle (cap, needle, and syringe) held within the capturing core.
Figure 1B:
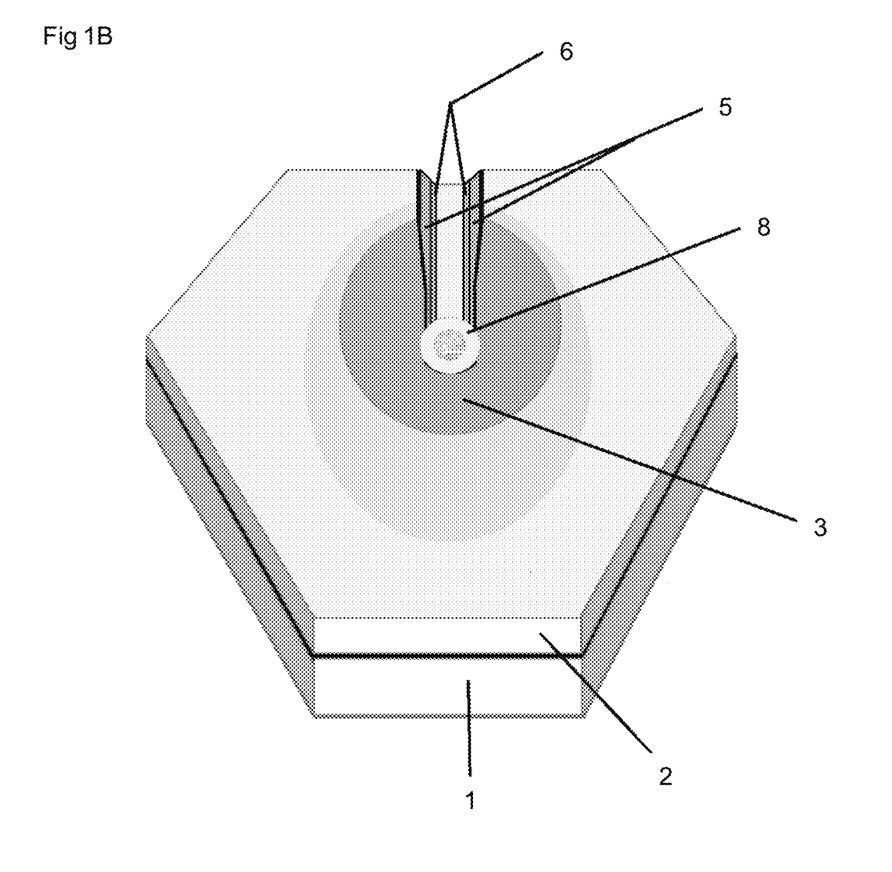
FIG. 1B is the same view as FIG. 1A, with the needle uncapped and the needle cap remaining in the capturing core.
Figure 1C:
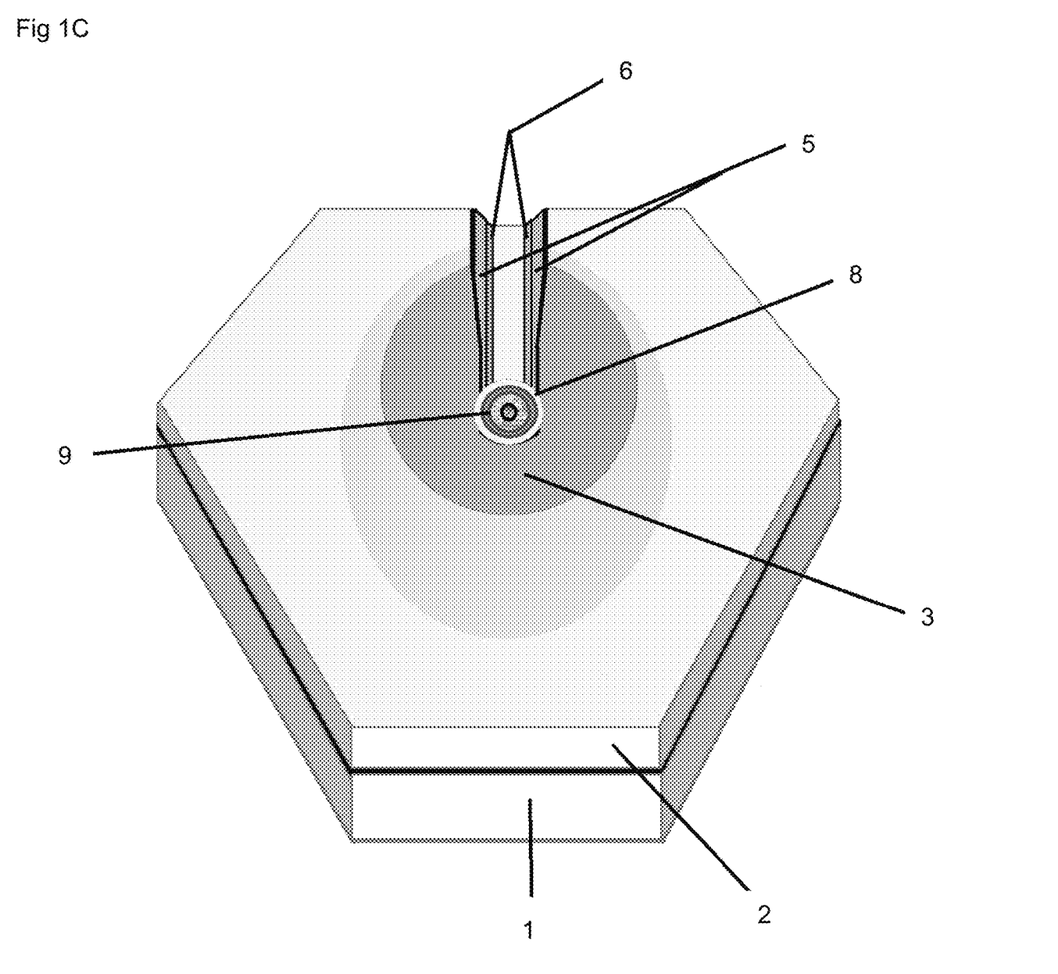
FIG. 1C is the same view as FIG. 1A, with the needle being interchanged, so the needle and cap are retained in the capturing core and the body of the syringe is absent.
Figure 2:
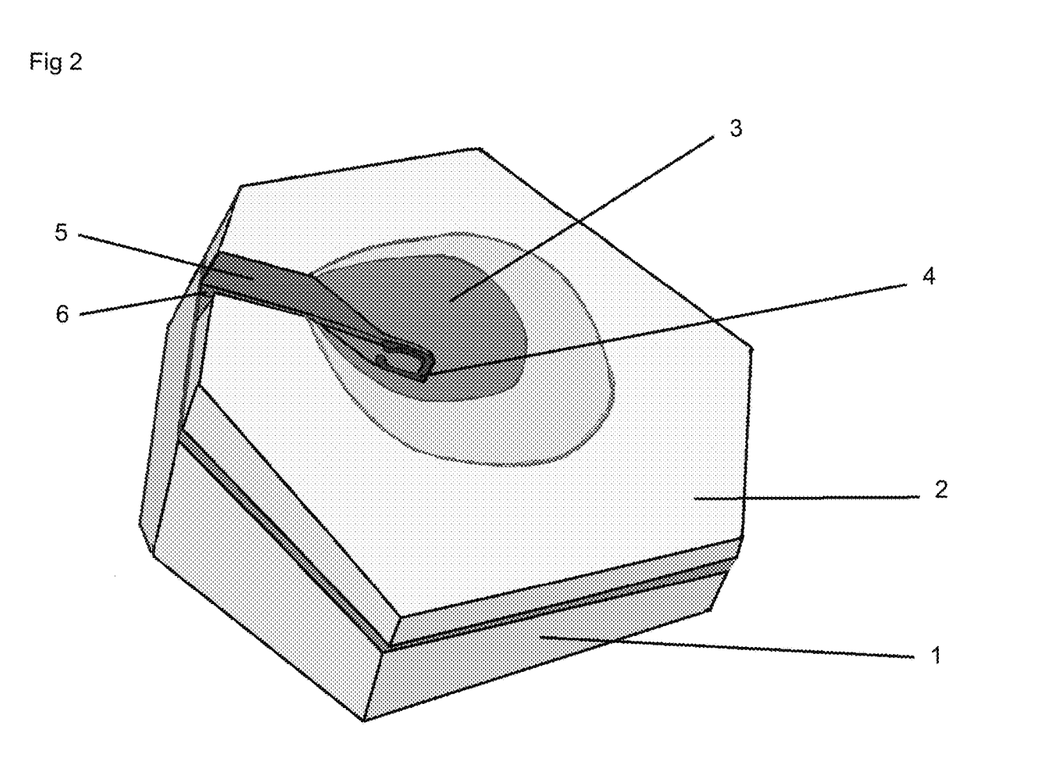
FIG. 2 is a left perspective (top) view of the invention.
Figure 2A:
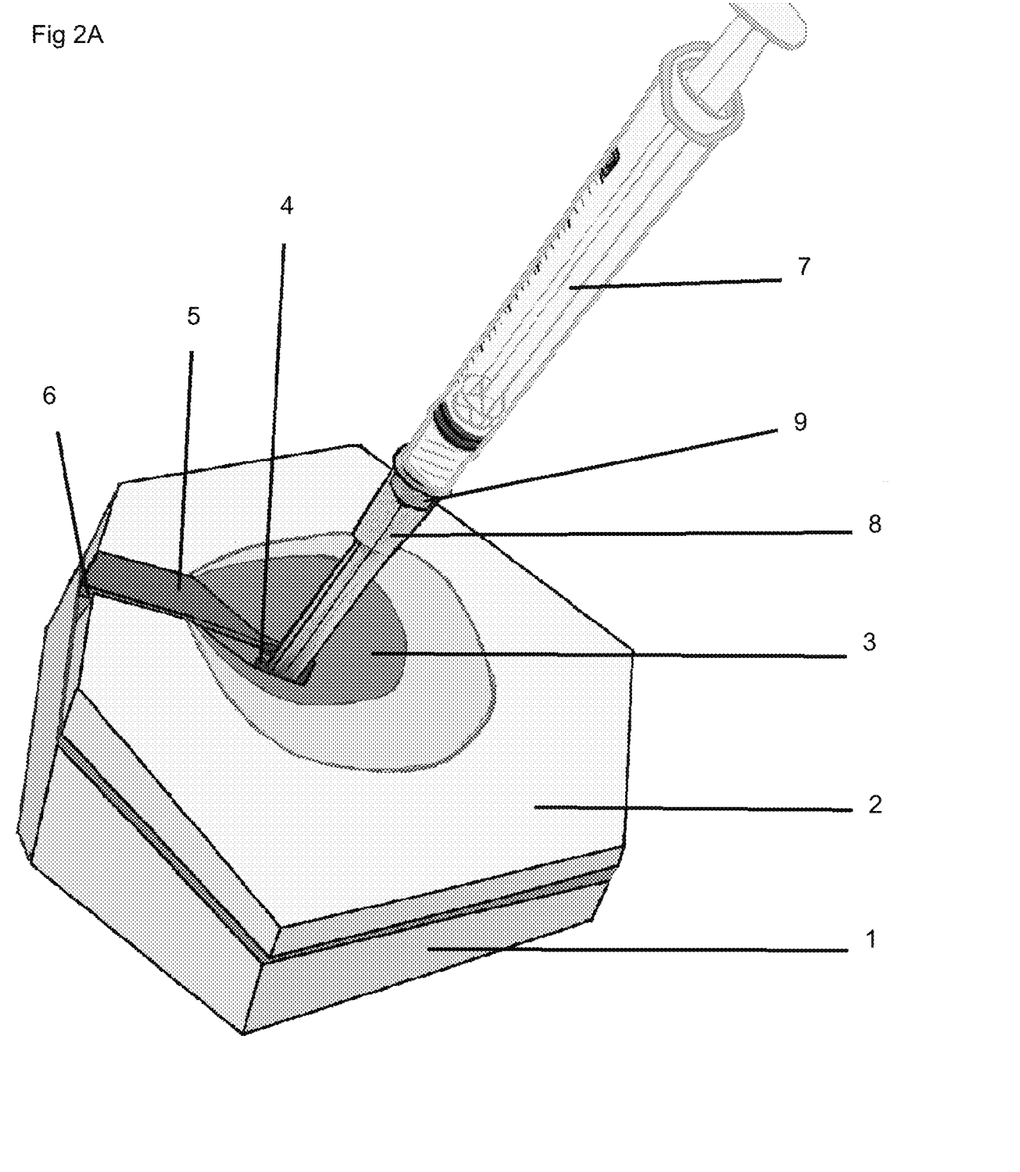
FIG. 2A is the same view as FIG. 2, with the apparatus in use with the entire needle (cap, needle, and syringe) held within the capturing core.
Figure 2B:
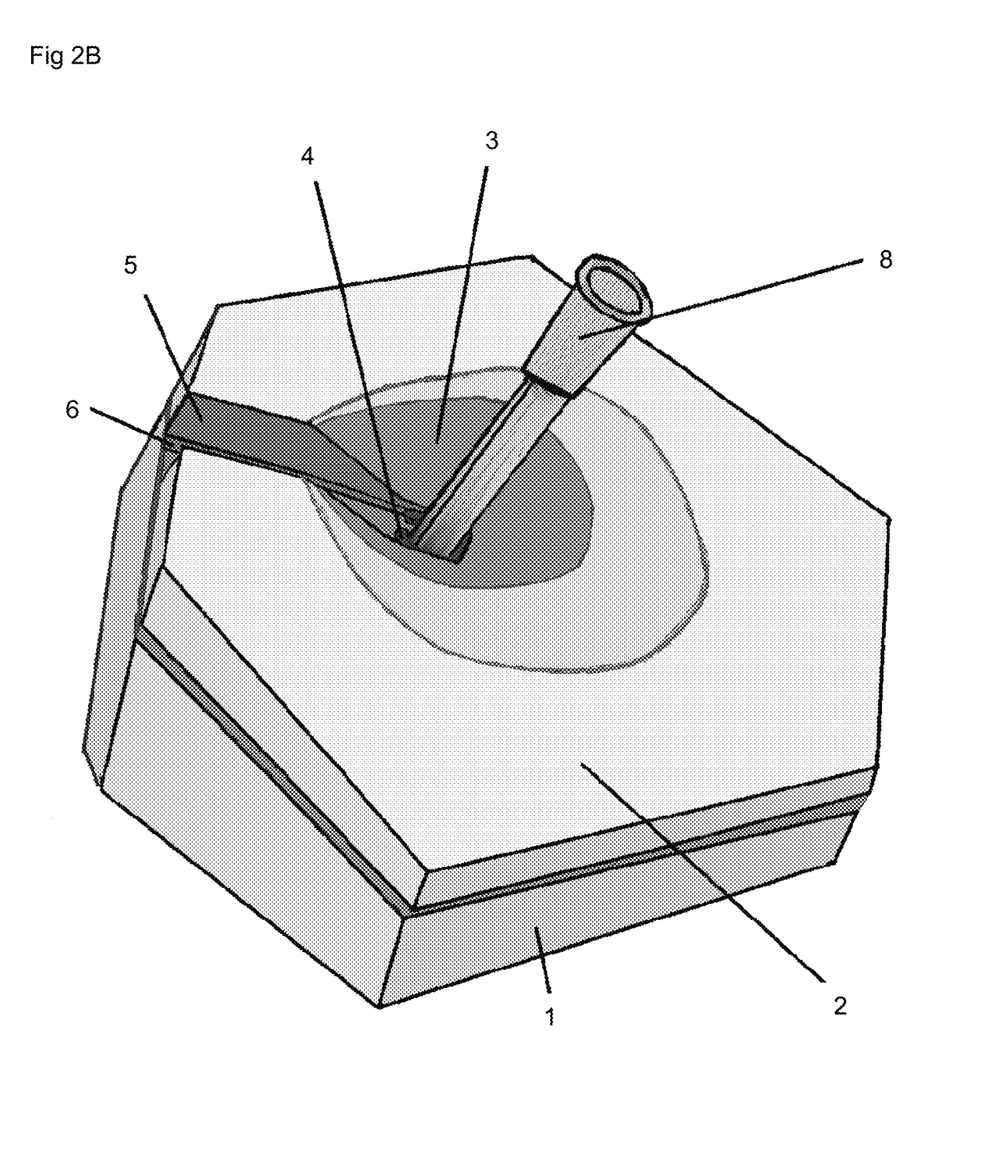
FIG. 2B is the same view as FIG. 2A, with the needle uncapped and the needle cap remaining in the capturing core.
Figure 2C:
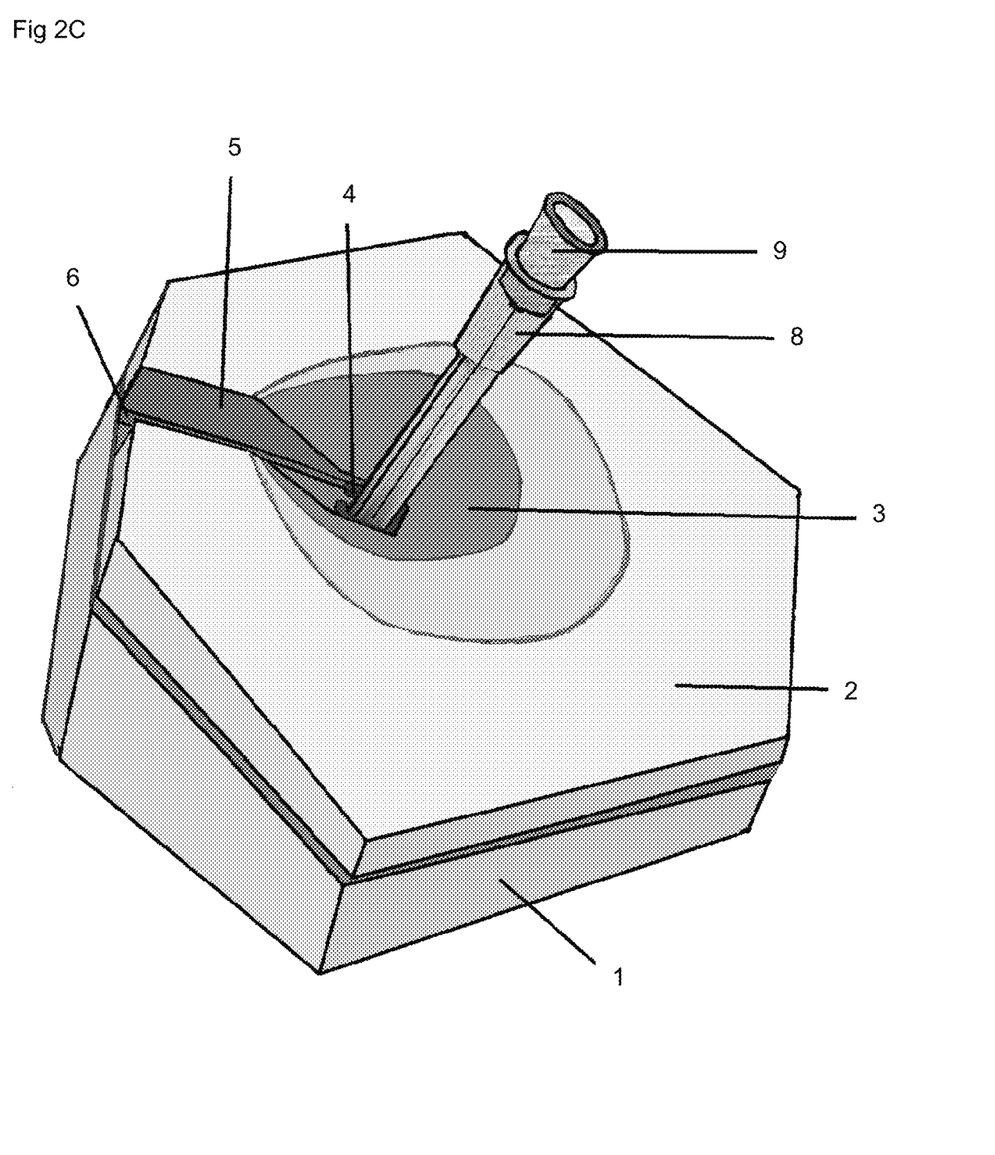
FIG. 2C is also the same view as FIG. 2A, with the needle being interchanged, so the needle and cap are retained in the capturing core and the body of the syringe is absent.
Figure 3:
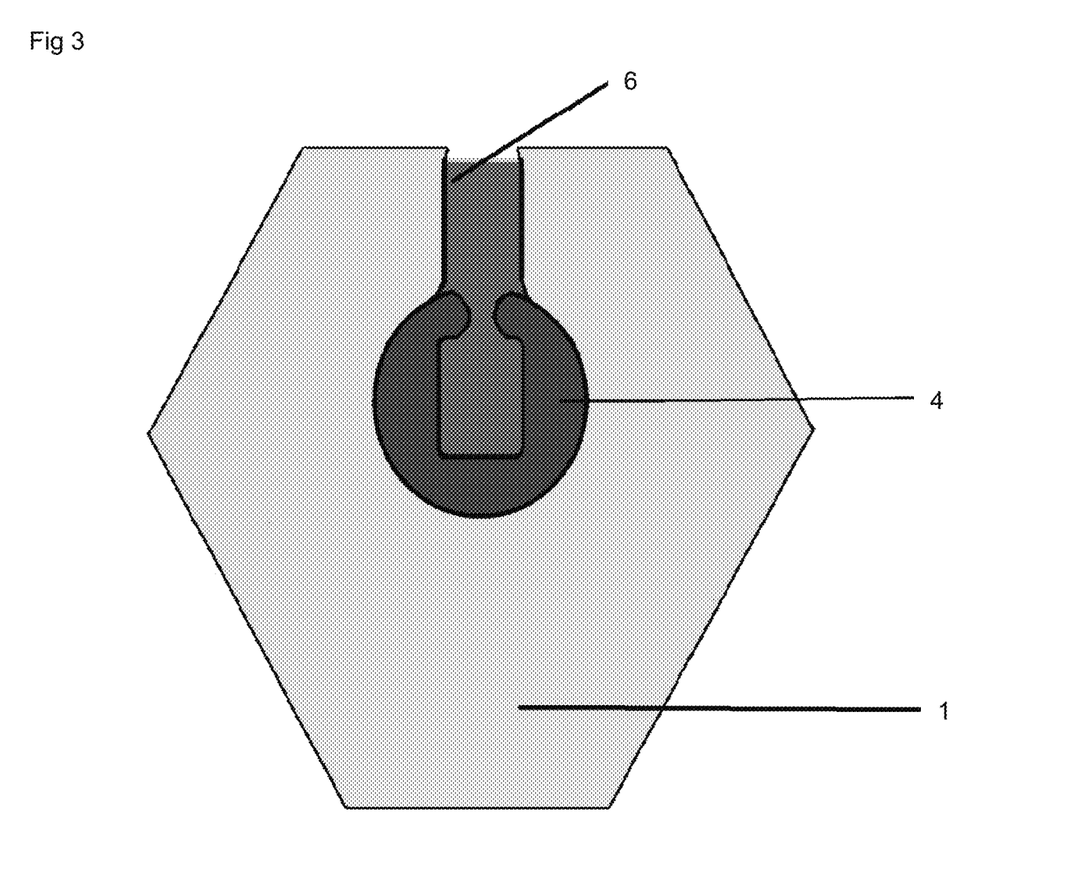
FIG. 3 is a top view of the base of the device, and has the capture core installed.
Figure 3A:
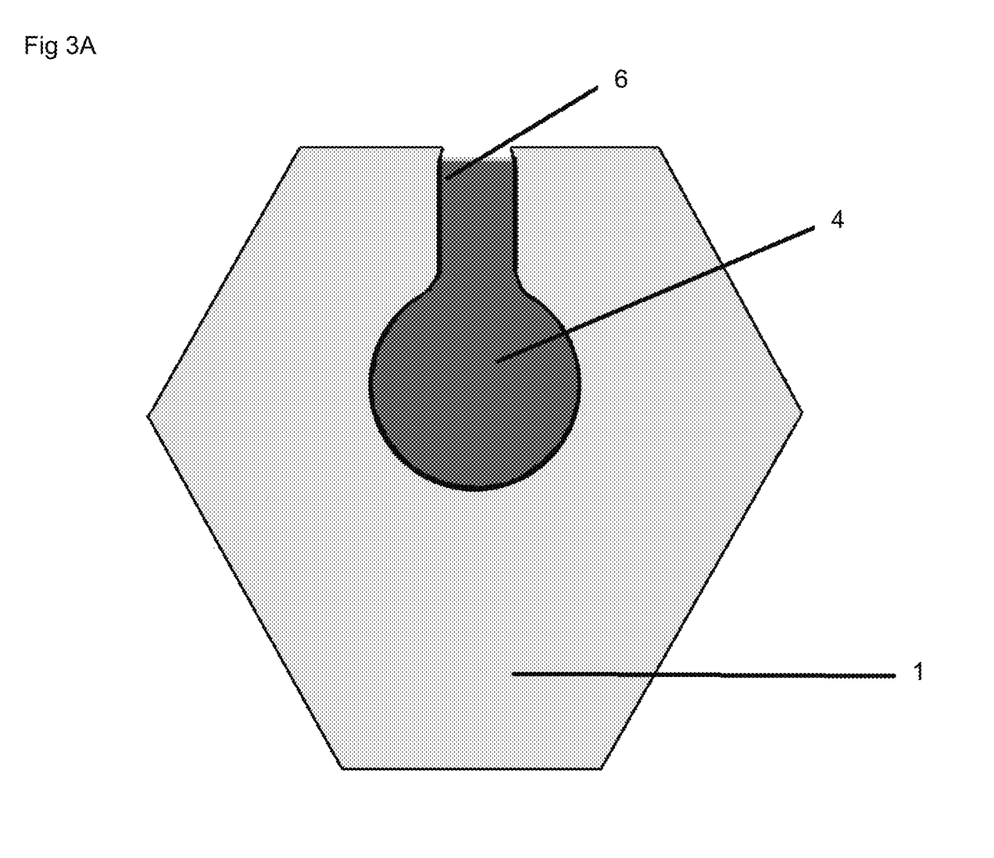
FIG. 3A is the same view as FIG. 3 with the capture core removed.
Figure 4:
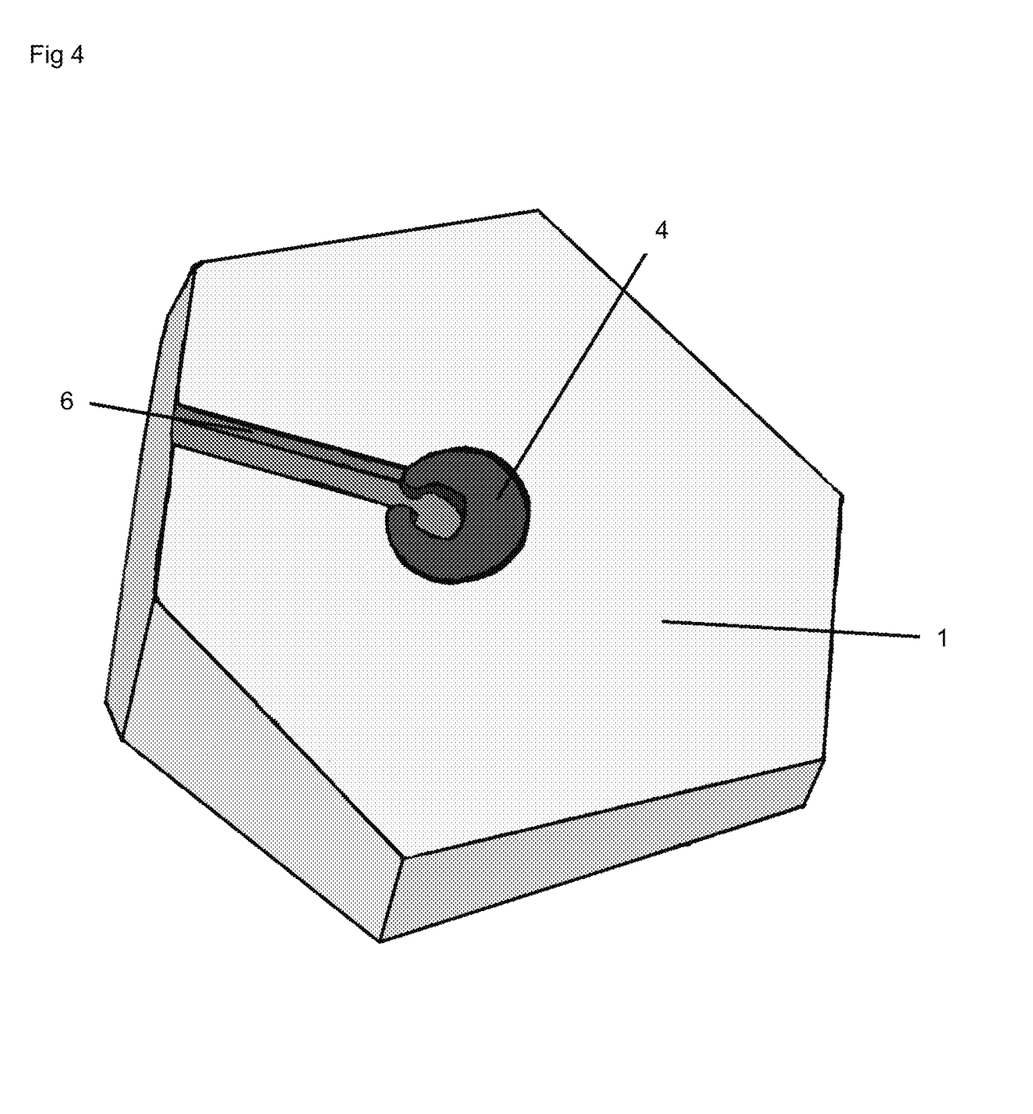
FIG. 4 is a perspective (top-left) view of the base of the device with the capture core installed.
Figure 4A:
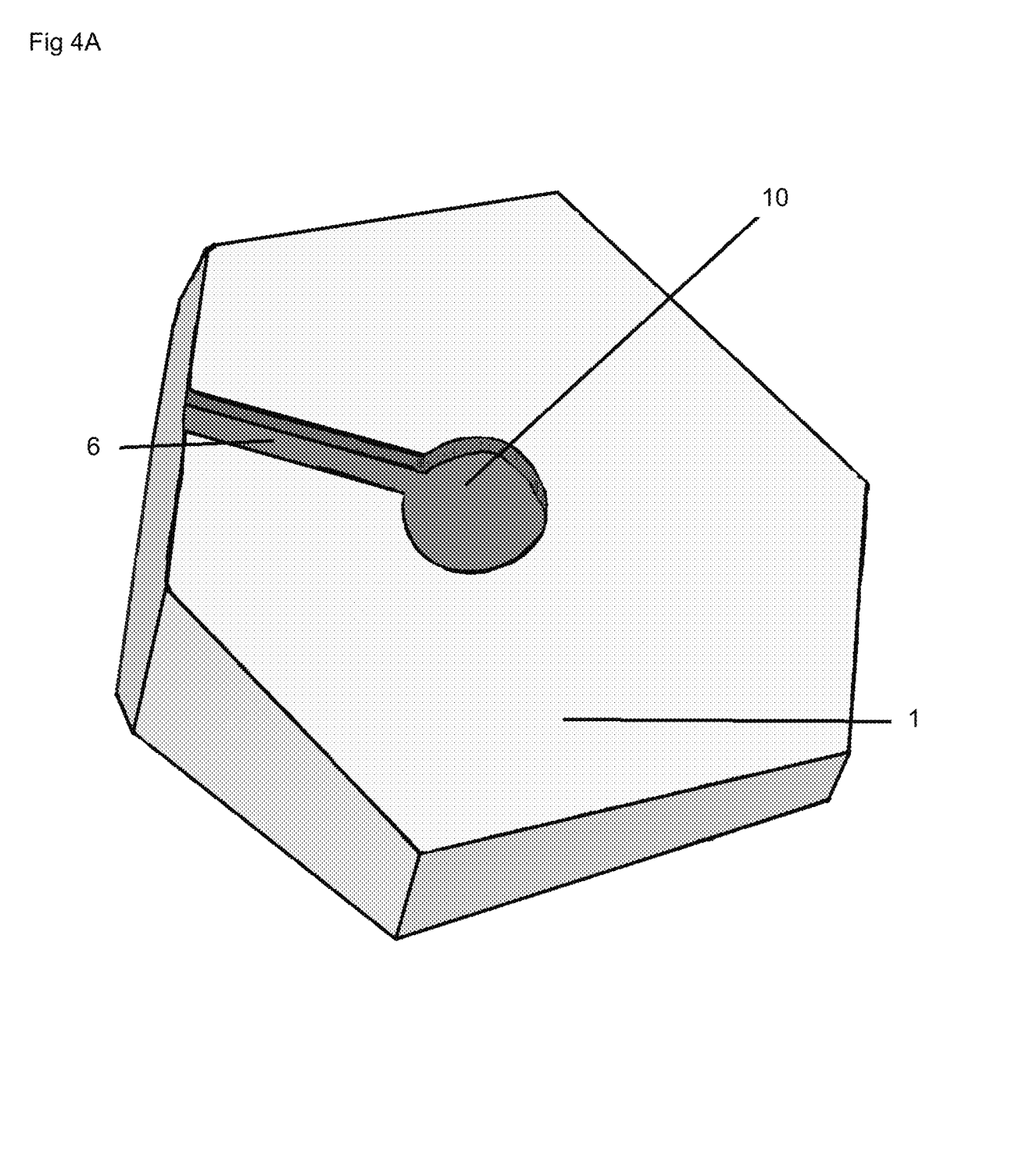
FIG. 4A is the same view as FIG. 4 with the capture core removed.
Figure 5:
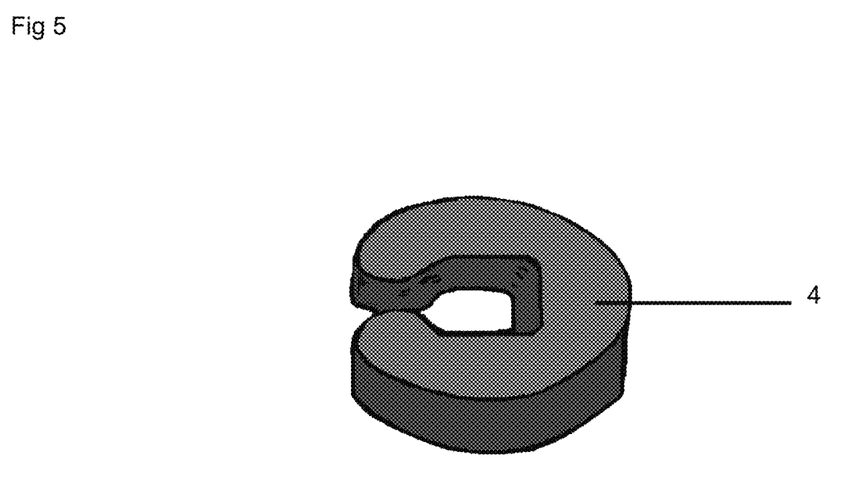
FIG. 5 is a perspective (top-left) view of the capture core.
Figure 5A:
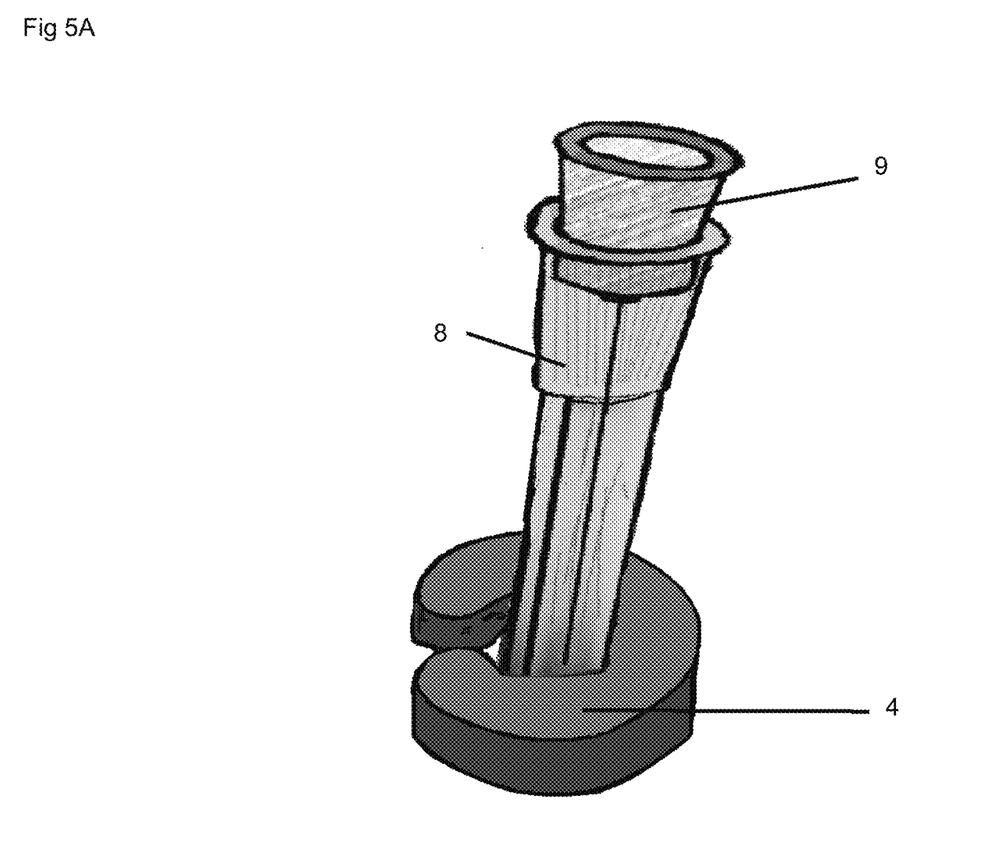
FIG. 5A is the same view as FIG. 5 with a cap and needle captured in the core.
Figure 6:
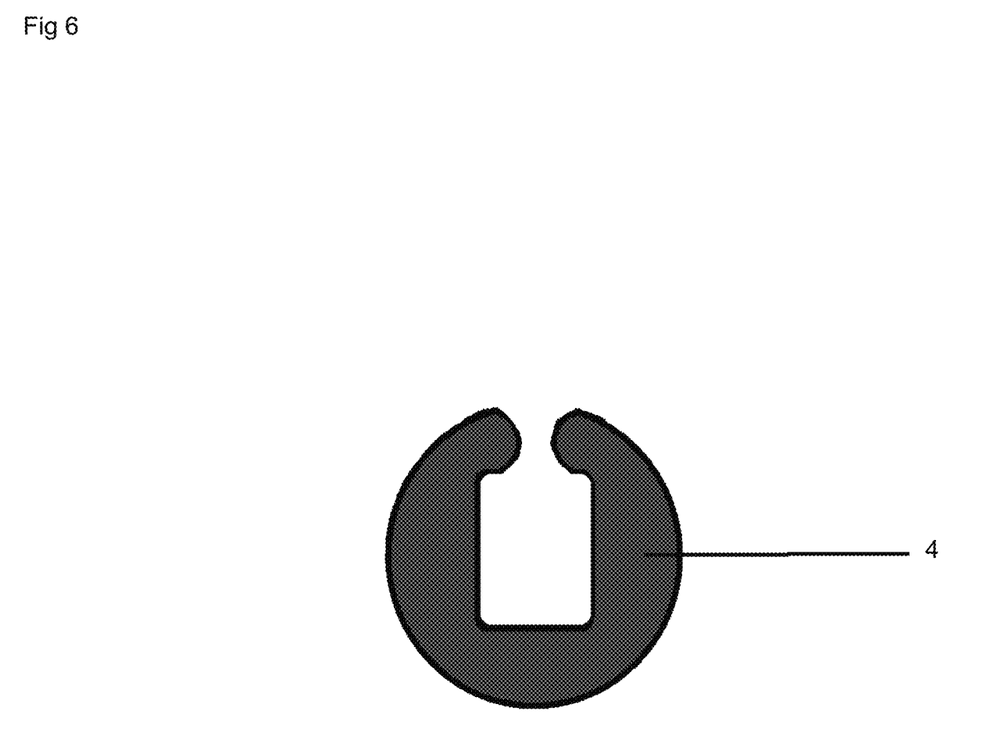
FIG. 6 is a top view of the capture core.
Figure 7:
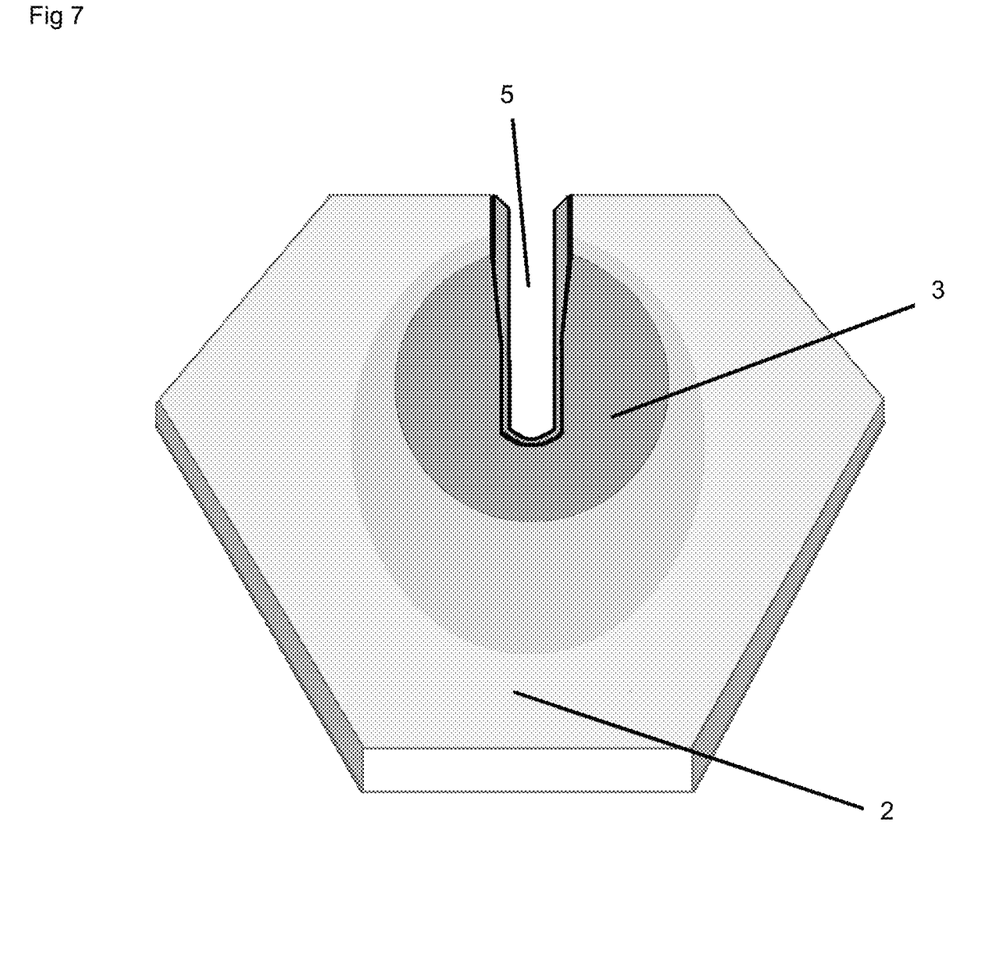
FIG. 7 is a top view of the removable top.
Figure 8:
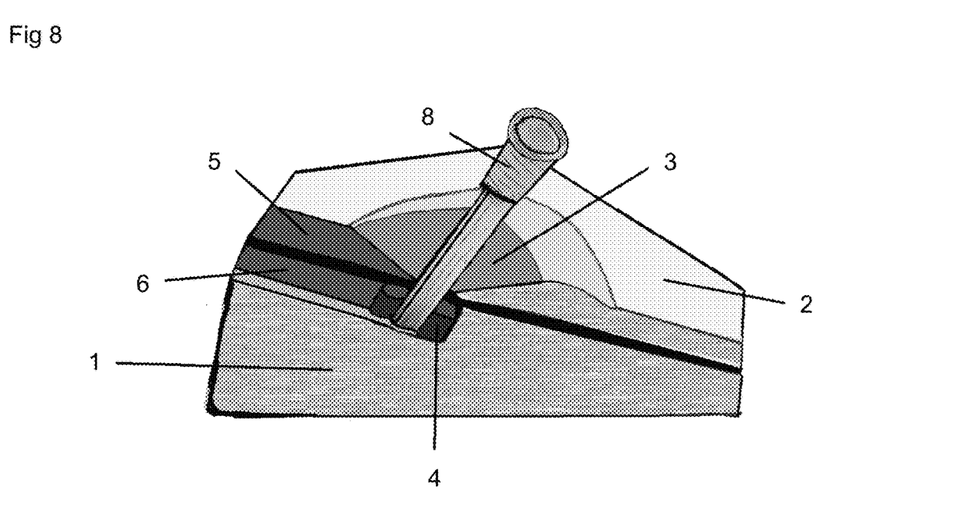
FIG. 8 is a perspective cross sectional view (top-left) of the device it has a needle cap captured in the capture core.

FIG. 1 through FIG. 8 of the drawings show an embodiment of an apparatus in accordance with the present description. Reference numeral 1 represents the weighted base of the device. Reference numeral 2 represents the removable device top. Reference numeral 3 represents a ramped surface built into the top surface of the base and top cap that guides the capped needle into the removable/replaceable capture core. Reference numeral 4 represents the cap gripping mechanism, also referred to as a capture core, made of a material able to accept, grip, and retain a capped needle, wherein the core accepts and grips the needle cap to allow for the safe uncapping recapping, interchanging and storage of needles. The cap gripping mechanism 4 has a "C" shaped profile that substantially circumscribes a central opening, and a channel at one end of the periphery of the cap gripping mechanism. Reference numeral 5 represents the tunnel built into the device top cap, which is present to allow for the needle to be safely removed one handed, the walls of the tunnel are distanced in a way as to allow them to be used as a tool, to allow the syringe to be twisted off while keeping the cap secure, ultimately allowing for the interchanging of needles. The Reference numeral 6 represents the tunnel built into the base of the device, it allows for a capped needle and syringe to be safely freed, with one hand, from the capture core without accidentally unsheathing it again. As shown in FIG. 3, the cap gripping mechanism 4 is positioned in the base such that the channel of the cap gripping mechanism is open to the tunnel 5. Reference numeral 7 represents any syringe. Reference numeral 8 represents any needle cap. Reference numeral 9 represents any needle. Reference numeral 10 represents the centrally located space built into the base to accept the capture core. The tunnel 6 extends laterally from the centrally located space. Reference numeral 11 represents a fully assembled hypodermic needle, with the syringe, needle, and cap present and assembled.

Figure 9:
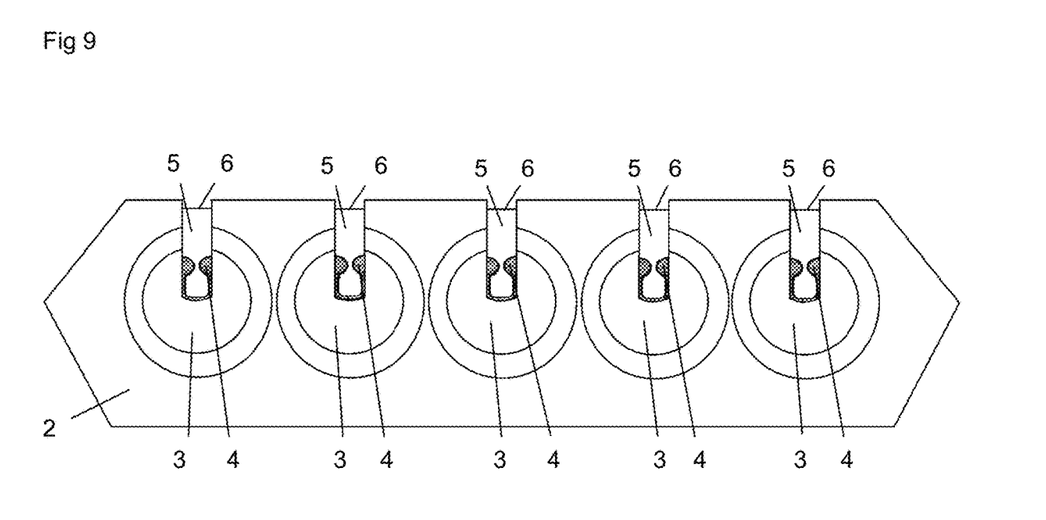
FIG. 9 is a top view of an alternative embodiment of the device in a format that can house multiple capture cores, useful in settings where the simultaneous usage of multiple needles is necessary.

FIG. 9 is a top view of an alternative embodiment of the device that can house multiple capture cores for use with multiple needle assemblies.

In an embodiment, the base, base top, and capture core are made of a material capable of withstanding sterilization via all acceptable methods.

What is claimed is:

1. An apparatus for the safe management of hypodermic needles, comprising:
a weighted base with a centrally located space to allow for secure placement of a compliant needle cap gripping mechanism, the centrally located space located within an opening in a top surface of the weighted base, the weighted base further comprising a tunnel extending laterally from the centrally located space, the tunnel being open to the top surface of the base;
the needle cap gripping mechanism having a "C" shaped profile with a central opening configured to be aligned with the opening in the top surface when positioned in the centrally located space so as to allow for a needle cap to be inserted longitudinally into and captured within the central opening, the needle cap gripping mechanism comprising a channel at a periphery of the "C" shaped profile such that the central opening is exposed to the tunnel within the base through said channel, the "C" shaped profile shaped to substantially circumscribe the central opening so as to retain the needle cap when inserted into the base;
wherein the channel is configured to allow one-handed manual lateral motion of the needle cap out of the central opening and into the tunnel to allow for a re-capped needle to be safely removed from the base while in a capped state.

2. The apparatus of claim 1, wherein the opening in the top surface of the base comprises a ramped opening to guide the needle cap to pass through and be captured by the cap gripping mechanism.

3. The apparatus of claim 1, further comprising: a top cap configured to be disposed over the base to secure the needle cap gripping mechanism in the base.

4. The apparatus of claim 1, wherein the central opening of the needle cap gripping mechanism comprises internal surfaces to fix the needle cap against rotation about the longitudinal axis of the needle cap such that a needle may be twisted to free the needle from the needle cap.

5. The apparatus of claim 1:
wherein the central opening of the needle cap gripping mechanism is sized and sufficiently compliant so as to secure the needle cap within the base even under longitudinal loading generated from pulling the re-capped needle from the base; and
wherein the tunnel has a width larger than the central opening of the needle cap gripping mechanism so that the re-capped needle may move freely in the tunnel and be extracted from the base with the needle cap attached.

* * * * *